(12) United States Patent
Gore et al.

(10) Patent No.: US 8,679,554 B2
(45) Date of Patent: Mar. 25, 2014

(54) ARTIFICIAL TEARS AND THERAPEUTIC USES

(71) Applicant: Allergan, Inc., Irvine, CA (US)

(72) Inventors: Anuradha V. Gore, Aliso Viejo, CA (US); Robert S. Jordan, Trabuco Canyon, CA (US); Kevin Krock, Corona, CA (US); Chetan Pujara, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/931,281

(22) Filed: Jun. 28, 2013

(65) Prior Publication Data

US 2013/0295206 A1 Nov. 7, 2013

Related U.S. Application Data

(63) Continuation of application No. 13/376,374, filed as application No. PCT/US2010/037153 on Jun. 3, 2010, now Pat. No. 8,496,976.

(60) Provisional application No. 61/184,339, filed on Jun. 5, 2009.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

| | | | |
|---|---|---|---|
| 4,649,047 A | 3/1987 | Kaswan | |
| 4,839,342 A | 6/1989 | Kaswan | |
| 5,411,952 A | 5/1995 | Kaswan | |
| 5,474,979 A | 12/1995 | Ding | |
| 5,981,607 A | 11/1999 | Ding | |
| 2006/0106104 A1 | 5/2006 | Vehige | |
| 2008/0070834 A1 | 3/2008 | Chang et al. | |

FOREIGN PATENT DOCUMENTS

| | | |
|---|---|---|
| EP | 1044678 A1 | 10/2000 |
| WO | 2008-027341 A2 | 3/2008 |
| WO | 2008-106228 A2 | 9/2008 |

OTHER PUBLICATIONS

Hom, et al., Understanding Emulsion Eye Drop Technology, Review of Optometry, 2008, 5 pages, http:www.revoptom.com/index.asp-page+2_888.htm, US.
Jumaa, et al., Mixture experiments with the oil phase of parenteral emulsions, European Journal of Pharmaceutics and Biopharmaceutics, 1998, 161-167, 46, US.
Jumaa, et al., The effect of oil components and homogenization conditions on the physicochemical properties and stability of parenteral fat emulsions, International Journal of Pharmaceutics, 1993, 81-39; 163, US.
Rashid, et al., Topical Omega-3 and Omega-6 Fatty Acids for Treatment of Dry Eye, Arch Ophthalmol, 2008, 219-225, 126, Laboratory Sciences, US.
Santosh Khanal, et al., Effect of an Oil-in-Water Emulsion on the Tear Physiology of Patients With Mild to Moderate Dry Eye, Cornea, Feb. 2007, 175-181, 26 (2), US.
Thompson, C:IEPOPROGS\SEA\.\..\..\epodata\seaepolgf\internal. log, 1981, (2 pages).
Vieira, et al., Effect of ricinoleic acid in acute and subchronic experimental models of inflammation, Mediators of Inflammation, 2000; 223-228, 9.
Patent Cooperation Treaty, The International Search Report and Written Opinion of the International Searching Authority, Jan. 13, 2011.

*Primary Examiner* — Michael Meller
(74) *Attorney, Agent, or Firm* — Lorenz Siddiqi

(57) ABSTRACT

The present invention provides ophthalmic compositions, e.g. artificial tears, suitable for treating dry eye syndrome in a human or other mammal suffering there from, e.g. a dog or cat, which comprise a mixture of castor oil with another oil, e.g. a food oil, e. g. olive oil, sesame oil, corn oil etc.

1 Claim, 1 Drawing Sheet

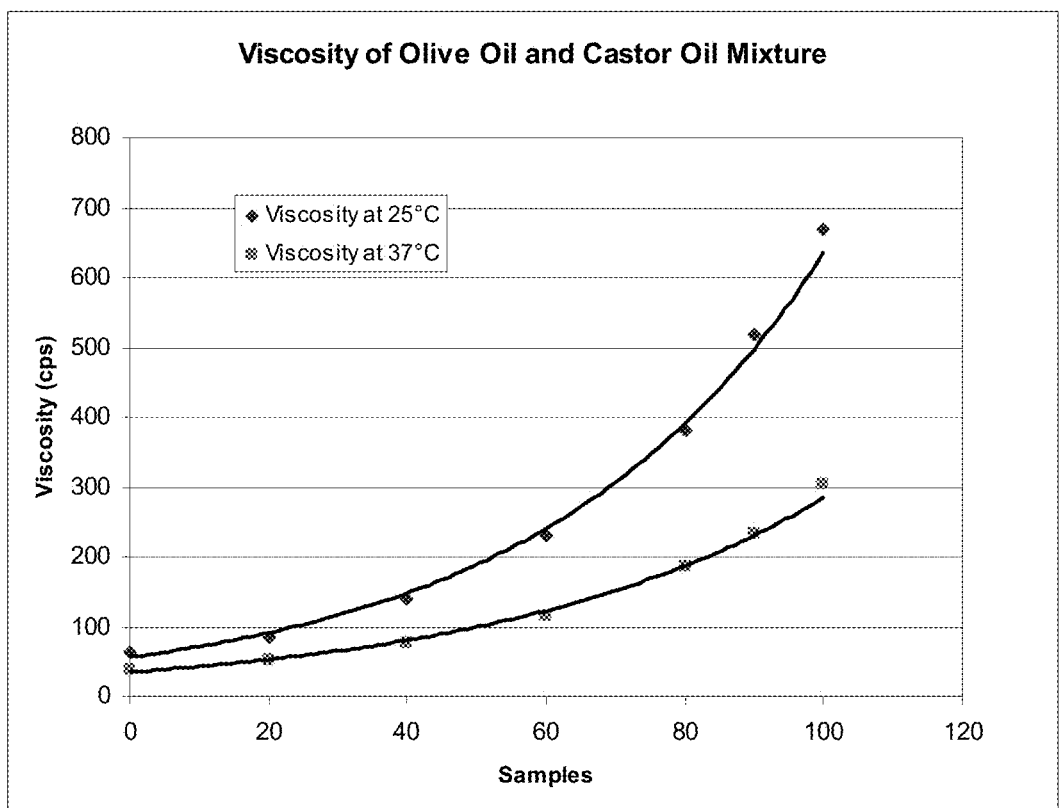

ARTIFICIAL TEARS AND THERAPEUTIC USES

CROSS-REFERENCE

This application is a continuation of U.S. patent application Ser. No. 13/376,374, filed Dec. 5, 2011, which is a national stage application under 35 U.S.C. §371 of PCT Patent Application Ser. No. PCT/US10/37153, filed Jun. 3, 2010, which claims the benefit of U.S. Provisional Patent Application Ser. No. 61/184,339, filed Jun. 5, 2009, all of which are hereby incorporated by reference in their entirety.

BACKGROUND OF THE INVENTION

1. Field of the Invention

The present invention is directed to artificial tears suitable for treating dry eye syndrome in a human or other mammal which comprises a mixture of castor oil with at least one other oil, for example a naturally occurring oil (e. g. olive oil, sesame oil, corn oil, etc.)

2. Description of Related Art

Typical symptoms of keratoconjunctivitis or dry eye include feelings of dryness, burning, and a sandy-gritty eye sensation that can worsen during the day. Symptoms may also be described as itchy, scratchy, stingy or tired eyes. Other symptoms include pain, redness, a pulling sensation, and pressure behind the eye. The damage to the eye surface resulting from dry eye increases discomfort and sensitivity to bright light and both eyes usually are affected.

Because blinking coats the eye with tears, symptoms are worsened by activities in which the rate of blinking is reduced due to prolonged use of the eyes. These activities include prolonged reading, computer usage, driving or watching television. Symptoms increase in windy, dusty or smoky areas, in dry environments, high altitudes including airplanes, on days with low humidity, and in areas where an air conditioner, fan, or heater, is being used. Symptoms are less severe during cool, rainy, or foggy weather, and in humid places. Most people who have dry eyes experience mild irritation with no long-term effects. However, if the condition is left untreated or becomes severe, it can produce complications that can cause eye damage, resulting in impaired vision or possibly in the loss of vision.

Having dry eyes for a prolonged period of time can lead to tiny abrasions on the surface of the eyes. In advanced cases, the epithelium undergoes pathologic changes, namely squamous metaplasia and loss of goblet cells sometimes due to activation of T cells directed. Some severe cases result in thickening of the corneal surface, corneal erosion, punctate keratopathy, epithelial defects, corneal ulceration, corneal neovascularization, corneal scarring, corneal thinning, and even corneal perforation. An abnormality of any one of the three layers of tears which produces an unstable tear film, may result in symptoms of keratitis sicca.

Keratoconjunctivitis sicca is usually due to inadequate tear production. The aqueous tear layer is affected, resulting in aqueous tear deficiency or lacrimal hyposecretion. The lacrimal gland does not produce sufficient tears to keep the entire conjunctiva and cornea covered by a complete layer. This usually occurs in people who are otherwise healthy. Increased age is associated with decreased tearing. This is the most common type found in postmenopausal women. Causes include idiopathic, congenital alacrima, xerophthalmia, lacrimal gland ablation, and sensory denervation. In rare cases, it may be a symptom of collagen vascular diseases, including rheumatoid arthritis, Wegener's granulomatosis, and systemic lupus erythematosus. Sjögren's syndrome and autoimmune diseases associated with Sjögren's syndrome are also conditions associated with aqueous tear deficiency. Drugs such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine can cause or worsen this condition. Infiltration of the lacrimal glands by sarcoidosis or tumors, or postradiation fibrosis of the lacrimal glands can also cause this condition.

Keratoconjunctivitis sicca can also be caused by abnormal tear composition resulting in rapid evaporation or premature destruction of the tears. When caused by rapid evaporation, it is termed evaporative dry eyes. In this condition, although the tear gland produces a sufficient amount of tears, the rate of evaporation of the tears is too rapid. There is a loss of water from the tears that results in tears that are too "salty" or hypertonic. As a result, the entire conjunctiva and cornea cannot be kept covered with a complete layer of tears during certain activities or in certain environments.

Aging is one of the most common causes of dry eyes. This is due to the fact that tear production decreases with age. It may be caused by thermal or chemical burns, or by adenoviruses. Diabetics are also at increased risk for dry eye.

An eye injury or other problem with the eyes or eyelids, such as bulging eyes or a drooping eyelid, can cause keratoconjunctivitis sicca. Disorders of the eyelid can impair the complex blinking motion required to spread tears.

About half of all people who wear contact lenses have dry eyes. This is because soft contact lenses, which float on the tear film that covers the cornea, absorb the tears in the eyes. Dry eye also occurs or gets worse after refractive surgeries, in which the corneal nerves are cut during the creation of a corneal flap, because the corneal nerves stimulate tear secretion. Dry eyes caused by these procedures usually disappear after several months.

Abnormalities of the lipid tear layer caused by blepharitis and rosacea, and abnormalities of the mucin tear layer caused by vitamin A deficiency, trachoma, diphtheric keratoconjunctivitis, mucocutaneous disorders and certain topical medications may cause dry eye or keratoconjunctivitis sicca.

Dry eyes can usually be diagnosed by the symptoms alone. Tests can determine both the quantity and the quality of the tears. A slit lamp examination can be performed to diagnose dry eyes and to document any damage to the eye. A Schirmer's test can measure the amount of moisture bathing the eye. This test is useful for determining the severity of the condition.

A variety of approaches can be taken to treatment, such as: avoidance of exacerbating factors, tear stimulation and supplementation, increasing tear retention, and eyelid cleansing and treatment of eye inflammation.

For mild and moderate cases, supplemental lubrication is the most important part of treatment. Application of artificial tears every few hours can provide temporary relief.

Lubricating tear ointments can be used during the day, but they generally are used at bedtime due to poor vision after application. They contain white petrolatum, mineral oil, and similar lubricants. They serve as a lubricant and an emollient. Depending on the severity of the condition, ointments may be applied from every hour to just at bedtime. Ointments should not be used with contact lenses. Inflammation occurring in response to tears film hypertonicity can be suppressed by mild topical steroids or with topical immunosuppressants such as cyclosporine.

Topical 0.05% cyclosporine A, as a castor oil-based ophthalmic emulsion, is marketed in the United States by Allergan under the trade mark RESTASIS®. RESTASIS® decreases surface inflammation of the eye. It is thought to work through inhibition of transcription factors required for cytokine production and T-lymphocyte maturation. In a trial involving 1200 people, RESTASIS® increased tear production in 15% of people, compared to 5% with placebo. Usually, 1 drop of RESTASIS® is instilled in each eye twice a day, 12 hours apart.

BRIEF SUMMARY OF INVENTION

The present invention provides artificial tears which comprise a blend or mixture of castor oil with another oil, i.e. a food oil or healthy oil, such as olive oil, sesame oil, corn oil, soybean oil, safflower oil, cottonseed oil, peanut oil, etc. Such blend of oils may be emulsified or dispersed in an aqueous phase, e.g. water, to provide a composition suitable for topical application to the eye of a mammal, suffering from dry eye, to relieve the symptoms thereof. Furthermore, the present invention provides a method for treating keratoconjunctivitis sicca (KCS) comprising providing the above composition, and administering said composition topically to the ocular surface or immediate vicinity of an eye of a patient.

BRIEF DESCRIPTION OF DRAWINGS

FIG. 1 shows the viscosities of varying mixtures of castor oil and olive oil at 25 and 37° C. In this figure the x axis refers to the percent castor oil in the oil mixture.

DETAILED DESCRIPTION OF INVENTION

Castor oil may be used in ophthalmic emulsion formulations for treating diseases and conditions of the eye because of its spreading properties. For example, it is believed that this ability to spread on an aqueous surface enables castor oil to form a thin layer on the ocular surface thereby reducing evaporation and helping alleviate symptoms of dry eye. There is a high level of interest in using other oils (referred to as 'healthy oils' or food oils, such as olive oil) in ocular formulas for dry eye treatment. However the spreading ability of these oils was found to be poor as compared to castor oil. (Food oils or healthy oils are described in United States Patent Application Publication No. US2008/0070834 A1, which is hereby incorporated by reference.)

When a drop of castor oil is added over the surface of water or model tear solution, it spreads quickly, forming a thin layer on the surface of the aqueous fluid. In contrast, other oils, such as soybean oil, olive oil, safflower oil, corn oil, sesame oil, peanut oil and cotton seed oil do not spread over the surface of either water or model tear solution, even after overnight application.

It has now been surprisingly found that even small amounts of castor oil added to the 'healthy oils' improves the spreading properties of these oils. It is believed that the improvement in dispersion obtained by using the mixture of castor oil with healthy oils helps the delivery of these more desired oils when placed on the ocular surface in treatment of dry eye.

An additional benefit in using the above blend or mixture of oils is the reduction of viscosity of castor oil when combined with other, less viscous oils. Surprisingly, this drop in viscosity was found to be non-linear and allows for selection of a formula of oil mixtures, with improved spreading and lower viscosity which is favorable for use in treatment of dry eye.

The oil mixtures of this invention comprise at least 5%, by weight, castor oil preferably at least 20%, by weight, castor oil. In particular, the oil mixtures of this invention comprise from 5 to 80%, by weight, castor oil and from 20 to 95%, by weight, of another oil, selected from the group of healthy oils or food oils, e.g. an oil selected from the group consisting of soybean oil, olive oil, safflower oil, corn oil, sesame oil, peanut oil and cotton seed oil, more preferably from 20 to 80%, by weight, castor oil and from 20 to 80%, by weight, of said other oil.

Most preferably, the oil mixture of this invention comprises from 5 to 50%, by weight, castor oil and from 50 to 95%, by weight, of soybean oil, or the oil mixture of this invention comprises from 20 to 80%, by weight, castor oil and from 20 to 80%, by weight, olive oil, e.g. the oil mixture of this invention may comprise 70%, by weight, castor oil and 30%, by weight, olive oil The oil mixture is preferably delivered to the eye in the form of an emulsion, including a micro emulsion, or a dispersion of said oil in a continuous aqueous phase, i.e. as an emulsion comprising from about 0.1 to 50%, by weight, oil and from 99.9 to 50%, by weight, of the aqueous phase, more preferably from about 0.1 to about 30%, by weight, oil and from about 99.9 to 70%, by weight, of the aqueous phase, e.g. about 0.25%, by weight, oil and about 99.75%, by weight, of the aqueous phase.

The emulsions of this invention may be prepared according to methods known in the art. For example, emulsions may be prepared by methods disclosed in U.S. Pat. Nos. 4,649,047; 4,839,342 and 5,411,952 wherein emulsions of castor oil are disclosed. That is, the emulsions of this invention are prepared by the methods disclosed in U.S. Pat. Nos. 4,649,047; 4,839,342 and 5,411,952 wherein the above oil mixtures are substituted for castor oil. Such patents are hereby incorporated by reference herein.

As disclosed in U.S. Pat. Nos. 4,649,047; 4,839,342 and 5,411,952, said emulsions of castor oil are disclosed as vehicles for cyclosporine. Similarly, the oil mixtures of the present invention may be used as vehicles for cyclosporine. Such patents are hereby incorporated by reference herein.

In addition, U.S. Pat. No. 5,474,979 discloses methods of preparing emulsions that are useful in treating dry eye. The emulsions of this patent are prepared by use of surfactants and dispersing agents which are especially suitable for preparing the emulsions of this invention. Such patent is hereby incorporated by reference herein.

Finally, US Patent Application Publication Number US2006/0106104 A1 discloses ophthalmic compositions which include compatible solute components, for example tonicity components, such as polyols and amino acids and, in particular, glycerin (glycerol), erythritol and carnitine. The ophthalmic compositions of this published patent application are useful for treating eyes that are exposed to hypertonic insult and, also, in a method of improving the visual acuity of a person in need thereof which comprises topically administering to said person, in an effective amount, said ophthalmic composition comprising a mixture of castor oil dispersed in an aqueous carrier component; and an effective amount of a tonicity component comprising a material selected from a combination of compatible solute agents. For example, said combination of compatible solute agents may comprise two polyol components and one amino acid component and wherein said polyol components may be erythritol and glycerol and said amino acid component may be carnitine. In the embodiment of the present invention, wherein the compositions include the tonicity components disclosed in the published patent application and, in particular, when the tonicity components are erythritol, glycerol and carnitine, the compositions of this invention are useful for treating eyes that are exposed to hypertonic insult, Similarly, these tonicity components and, preferably, glycerin, erythritol and carnitine, may be included in the emulsions of this invention to provide an ophthalmic composition which may be applied topically to improve visual acuity. Such patent application is hereby incorporated by reference herein.

The compositions of this invention may be prepared as described in Example 1, below.

EXAMPLE 1

Manufacturing Procedure for Emulsion Compositions of this Invention

As disclosed below, the emulsion compositions of this invention may be manufactured with and without tonicity components, such as glycerin, erythritol, carnitine, etc.

Batches were manufactured on a weight basis from pre-weighed compendial raw materials in five parts:

Part 1: an oil phase containing a mixture of castor oil and olive oil (non-sterile).

Part 2: an aqueous phase containing purified water, polysorbate 80, and glycerin. Part 2 is sterile filtered using a sterile Nalgene filtration unit with a 0.2 μm PES membrane.

Part 3: an aqueous polymer dispersion containing purified water and Pemulen® TR-2 (5× Stock solution, 0.5%). Part 3 is sterilized by autoclaving at 121° C. for 15 minutes at 15 psig.

Part 4: an aqueous polymer dispersion containing purified water and sodium carboxymethylcellulose. (5× Stock solution, 2.5%). Part 4 is sterilized by autoclaving at 121° C. for 15 minutes at 15 psig.

Part 5: an aqueous phase containing purified water, erythritol, levocarnitine, boric acid, Sodium Hydroxide (pH adjustment), and purite (preservative). Part 5 is sterile filtered using a sterile Nalgene filtration unit with a 0.2 μm PES membrane. Part 5 can be modified based on formulation vehicle, see Table 1.

Procedure: Part 1 is added to Part 2 and the mixture is homogenized at 60°-70° C. for ~60 minutes at 14-15 Krpm. Part 1 and Part 2 is mixed using a Polytron PT 3100 homogenizer with a rotostator style tool (~30 mm head). The homogenizing step takes place in a laminar flow hood as do all subsequent manufacturing steps. The premix is cooled to 30° C. and Part 3 is added while mixing at low speed using a magnetic stir bar. Part 4 is then added while similarly mixing at a slow speed using a magnetic stir bar. Part 5 is added under light protection using a similar mode of mixing. The emulsion, protected from light from this point forward, is mixed at a low speed for a specified period of time (~30 minutes) to form the final bulk emulsion.

Following the manufacturing procedure as previously outlined, the following are combined:

Part 1 & 2: 800 g (oil/glycerin/PolySorbate 80)

Part 3: 400 g (0.5% (w/w) Pemulen TR-2—5× Stock)

Part 4: 400 g (2.5% (w/w) Na carboxymethylcellulose—5× Stock))

Part 5: 400 g (buffer/without ions/purite—5× Stock)

Batch Size: 2,000 g

TABLE 1

Composition of Emulsion

| Ingredients | 0.25% Castor/Olive Oil (70:30) |
|---|---|
| Ingredients | % (w/w) |
| PART 1 | |
| Castor/Olive Oil (70:30) | 0.25 |
| PART 2 | |
| Purified Water | ~40 |
| Polysorbate 80 | 0.5 |
| Glycerin | 1.0 |
| PART 3 (0.5% Stock Solution) | |
| Purified Water | ~20 |
| Pemulen TR-2 | 0.1 |
| PART 4 (2.5% Stock Solution) | |
| Purified Water | ~20 |
| Carboxymethylcellulose Sodium (Low Viscosity) | 0.5 |
| PART 5 (5X Stock Solution) | |
| Purified Water | ~20 |
| Boric Acid | 0.6 |
| Erythritol | 0.25 |
| Carnitine | 0.25 |
| Sodium Hydroxide, 5N | Adjust to pH 7.3 |
| Stabilized Oxychloro complex (Purite) | 0.01 |
| Purified Water | Q.S. |

The mixture of oils used in the ophthalmic compositions of this invention may be evaluated as described in Example 2, below.

EXAMPLE 2

Testing of Oil Mixtures for Ability to Spread on Ocular Surface Drop Dispersion Procedure 1. "Model Tear Solution", described in Table 2, below, is added to of a small cell culture dish (25 mm×10 mm style) in an amount sufficient to cover the bottom thereof Amount should be ~2.5 mL);
2. One drop of oil mixture (10 to 50 μl drop size) is added to said dish and an observation of how readily the drop disperses on the surface of the tear solution is made for not less then 60 seconds;
3. The drop dispersed on the tear solution surface is mixed with a spatula and how readily the drop disperses in the tear solution is observed; and,
4. The mixed oil and tear solution observe for several minutes/hours to see if oil coalesces.

TABLE 2

Composition of Model Tear Solution

| Ingredient | Conc. (% w/v) |
|---|---|
| Sodium Chloride | 0.90 |
| Calcium Chloride, Dihydrate | 0.015 |
| Sodium Phosphate Dibasic, Heptahydrate | 0.028 |
| Lysozyme, egg white | 0.19 |
| Albumin, bovine | 0.020 |
| Gamma-Globulin, human | 0.010 |
| Mucin, bovine submaxillary | 0.020 |
| 1N HCl and/or 1N NaOH | Adj. to pH 7.2 |
| Purified Water | Q.S. |

Using the above procedure the following oils and mixtures of oils are tested and the results reported in Table 3, below.

TABLE 3

Spreading behavior observed for oils when added to model tear solution

| Oil composition | | Observation after addition of 1 drop to model tear solution |
|---|---|---|
| Single oils | Castor oil | Drop disperses readily on contact with tear solution, remains dispersed overnight, no coalescence |
| | Soybean oil | Drop does not disperse, even after overnight time period |
| | Olive oil | Drop does not disperse, even after overnight time period |
| | Safflower oil | Drop does not disperse, even after overnight time period |
| | Corn oil | Drop does not disperse, even after overnight time period |
| | Sesame oil | Drop does not disperse, even after overnight time period |
| | Peanut oil | Drop does not disperse, even after overnight time period |
| | Cottonseed oil | Drop does not disperse, even after overnight time period |
| Oil mixture Castor oil + Soybean oil | 5:95 ratio | Drop disperses readily on contact with tear solution |
| | 10:90 ratio | Drop disperses readily on contact with tear solution |
| | 20:80 ratio | Drop disperses readily on contact with tear solution |
| | 50:50 ratio | Drop disperses readily on contact with tear solution |
| Oil mixture Castor oil + Olive oil | 20:80 ratio | Drop disperses readily on contact with tear solution |
| | 40:60 ratio | Drop disperses readily on contact with tear solution |
| | 60:40 ratio | Drop disperses readily on contact with tear solution |
| | 80:20 ratio | Drop disperses readily on contact with tear solution |

As shown in Table 2, The addition of minor amounts of castor oil, to an oil which does not spread on a model of the an ocular surface causes the spreading across ocular surface. In particular, the addition of as little as 5%, by weight, castor oil, to soybean oil causes the spreading of the resulting oil mixture across ocular surface. The addition of as little as 20%, by weight, castor oil, to olive oil causes the spreading of the resulting oil mixture across ocular surface.

The ophthalmic compositions of the present invention were evaluated in an in-vivo study as described in Example 3, below.

EXAMPLE 3

Summary of 1-Day Ocular Tolerability Study of an Emulsion of Example 2 in Rabbits A 1-day ocular tolerability study of an emulsion comprising 0.25%, by weight, of a 70/30 castor oil/olive oil mixture, manufactured according to Example 1, was conducted in rabbits. The oil mixture was utilized as a vehicle for the tonicity components carnitine, glycerine and erythritol. Female New Zealand White rabbits (5 rabbits/group) were given one drop (~40 µL each drop) of said emulsion of or a marketed, comparator eye drop, comprising 1.25%, by weight, castor oil, emulsified in an aqueous phase, by topical ocular instillation in the left eye (OS), 6 times daily (approximately 1 hr intervals) for one day. The contralateral right eye (OD) served as a control without eye drop instillation. The following parameters were evaluated: viability, clinical observations, ocular discomfort, gross ocular observations (irritation), and ophthalmic examination (slit lamp biomicroscopy, pupillary reflex). Ocular instillation of the emulsion of the invention caused a minimal discomfort response with duration of up to 30 sec (70% frequency) or 30 to 60 sec (7% frequency). The comparator eye drop caused a minimal discomfort response with duration of up to 30 sec (57% frequency) or 30 to 60 sec (13% frequency). There were no effects of ocular instillation of the above emulsion on gross ocular observations (irritation). The comparator eye drop, caused mild (+1) or moderate (+2) conjunctival congestion (hyperemia) with 50% or 3% frequency, respectively. In conclusion, the emulsion of this invention caused equivalent minimal, transient discomfort and significantly less mild conjunctival hyperemia compared to a marketed, comparator eye drop.

TABLE 4

Composition of Emulsion of Oil Mixture and Comparator Emulsion Formulations

| Ingredients | 0.25% Castor/Olive (70/30) % (w/w) | 1.25% Castor Oil % (w/w) |
|---|---|---|
| Castor Oil | 0.175 | 1.25 |
| Olive Oil, Super Refined (Croda) | 0.075 | — |
| Polysorbate 80, Super Refined (Croda) | 0.5 | — |
| Polysorbate 80 | — | 1.0 |
| Carboxymethylcellulose Sodium (Low Viscosity, 7LFPH) | 0.5 | — |
| Pemulen TR-2 | 0.1 | 0.1 |
| Glycerin | 1.0 | 1.0 |
| Purite | 0.01 | 0.0075 |
| Boric Acid | 0.6 | 0.6 |
| Erythritol | 0.25 | — |
| Levocarnitine | 0.25 | — |
| 5N NaOH and/or 5N NaOH | Ad pH to 7.3 | Ad pH to 7.3 |
| Purified Water | QS | QS |

The viscosity of mixtures of the oils used in the compositions and method of this invention were determined as described in Example 4, below.

EXAMPLE 4

Measuring the Viscosity of Mixtures of Castor Oil and Other Oils

Mixtures of Castor oil and olive oil were prepared and the viscosities thereof were determined The results are reported in FIG. 1. As shown. The change in viscosity is nonlinear, i.e. discontinuous. Surprisingly, small amounts of olive oil reduce the viscosity to a greater extent then larger amounts. That is, 10 and 20%, by weight, olive oil reduces the viscosity of castor oil from 675 cps to 510 cps and 390 cps at 25° C., respectively and from 305 cps to 230 cps and 195 cps at 37° C., respectively. By comparison, 60 and 40%, by weight, olive oil further reduces the viscosity of castor oil to 105 cps and 95 cps at 37° C., respectively, and 220 cps and 150 cps at 25° C., respectively, Thus, the advantages of using castor oil, alone, while substantially reducing the viscosity thereof is obtained by the addition of small amounts of another oil, e.g. olive oil.

The compositions of the invention can be administrated topically to various mammalian species suffering from dry eye, e.g., humans, cats, dogs and the like in an effective amount to relieve the symptoms of dry eye, as needed or on a regimen in single or 2 to 4 daily doses.

The foregoing description details specific methods and compositions that can be employed to practice the present invention, and represents the best mode contemplated. While the above invention has been described with reference to the compositions, above, the oils described below may be included within the scope of this invention:

linseed oil
eucalyptus oil.
sunflower oil.
peppermint oil.
rosemary oil.
caraway oil.
rapeseed oil.
maize oil.
cottonseed oil
arachis oil.
almond oil.

In addition, the above mixtures of castor oil with a healthy oil, may be advantageously, used in combination with various tonicity improving compounds. In particular, the combination of one of the oil mixtures, described above, with a tonicity component, may be used to treat dry eye and improve the visual acuity of a person in need of said treatment, by topically administering to said person, in an effective amount, an ophthalmic composition comprising said oil mixture dispersed in an aqueous carrier component; and an effective amount of a tonicity component comprising a material selected from a combination of compatible solute agents, wherein said combination of compatible solute agents comprises two polyol components and one amino acid component and wherein said polyol components are erythritol and glycerol and said amino acid component is carnitine.

Thus, however detailed the foregoing may appear in text, it should not be construed as limiting the overall scope hereof; rather, the ambit of the present invention is to be governed only by the lawful construction of the appended claims.

What is claimed is:

1. A method for treating keratoconjunctivitis sicca in a human in need thereof consisting of administering to said human in need thereof therapeutically effective amounts of a composition comprising:
   an oil mixture consisting essentially of linseed oil and castor oil;
   carboxymethyl cellulose;
   glycerin;
   polysorbate 80;
   crosslinked copolymers of acrylic acid and C10-C30 alkyl acrylate;
   polyoxyl stearate;
   carnitine;
   erythritol;
   boric acid; and,
   water.

* * * * *